(12) United States Patent
Mitschke

(10) Patent No.: US 6,585,412 B2
(45) Date of Patent: Jul. 1, 2003

(54) X-RAY CALIBRATION DUMMY, A METHOD FOR NON-MARKER-BASED REGISTRATION FOR USE IN NAVIGATION-GUIDED OPERATIONS EMPLOYING SAID X-RAY CALIBRATION DUMMY, AND A MEDICAL SYSTEM HAVING SUCH AN X-RAY CALIBRATION DUMMY

(75) Inventor: Matthias Mitschke, Nüruberg (DE)

(73) Assignee: Siemens Aktiengesellschaft, Munich (DE)

( * ) Notice: Subject to any disclaimer, the term of this patent is extended or adjusted under 35 U.S.C. 154(b) by 26 days.

(21) Appl. No.: 09/960,313

(22) Filed: Sep. 24, 2001

(65) Prior Publication Data

US 2002/0041655 A1 Apr. 11, 2002

(30) Foreign Application Priority Data

Sep. 25, 2000 (DE) .......................................... 100 47 382

(51) Int. Cl.$^7$ ................................................ G01D 18/00
(52) U.S. Cl. ...................................................... 378/207
(58) Field of Search ......................................... 378/207

(56) References Cited

U.S. PATENT DOCUMENTS

| 5,442,674 A | 8/1995 | Picard et al. | |
| 5,588,430 A | * 12/1996 | Bova et al. | ................. 378/207 |
| 6,379,043 B1 | * 4/2002 | Zylka et al. | ................. 378/207 |

* cited by examiner

*Primary Examiner*—Craig E. Church
(74) *Attorney, Agent, or Firm*—Young & Thompson

(57) ABSTRACT

An X-ray calibration dummy (RP) having markings (4) that may be acquired by a position-acquisition system (30). The invention also concerns a method for nonmarker-based registration for use in navigation-guided operations employing the X-ray calibration dummy (RP). A medical system for carrying out the method has a C-shaped X-ray machine (10), a position-acquisition system, 30, and the X-ray calibration dummy (RP).

16 Claims, 3 Drawing Sheets

X-RAY CALIBRATION DUMMY, A METHOD FOR NON-MARKER-BASED REGISTRATION FOR USE IN NAVIGATION-GUIDED OPERATIONS EMPLOYING SAID X-RAY CALIBRATION DUMMY, AND A MEDICAL SYSTEM HAVING SUCH AN X-RAY CALIBRATION DUMMY

An X-ray calibration dummy, a method for non-marker-based registration for use in navigation-guided operations employing said X-ray calibration dummy, and a medical system having such an X-ray calibration dummy.

BACKGROUND OF THE INVENTION

The invention concerns an X-ray calibration dummy having markings. The invention also concerns a method for non-marker-based registration for use in navigation-guided operations employing said X-ray calibration dummy, and a medical system having such an X-ray calibration dummy.

Navigation, which is defined as guiding a medical instrument relative to a living being or relative to that portion of the tissues of said living being receiving treatment with the aid of optical imaging information, where an image of the instrument is inserted into, for example, a 2D-image or 3D-image of the living being involved obtained using an X-ray machine, is increasingly being used to support medical procedures on living beings. This approach allows an operator to guide an instrument that has at least partially penetrated the living being and whose tip is no longer directly visible due to, for example, its having penetrated bodily tissues, based on imaging information relating to that portion of the tissues of the living being that is to be treated, without running the risk of inadvertently injuring the living being.

In order to make such navigation-guided operations possible, i.e., in order to be able to insert an accurately positioned and accurately oriented image of the instrument into imaging information on a living being, a mathematical relation in the form of a coordinate transformation between a coordinate system of the imaging information on the living being or a coordinate system of the reconstructed volume of the living being and a coordinate system used for stating the positions of the instrument to be navigated will have be generated. To this end, artificial markings are occasionally arranged on the living being or anatomical markings, e.g., prominent bone structures, are established. In this case, the anatomical or artificial markings must be clearly visible on X-ray images of the living being and readily accessible on the living being. The artificial markings are, e.g., attached to the surface of the skin of the living being, in order to allow what is known as their registration, which is defined as determining the rule for transforming the spatial coordinates defined for the coordinate system used for stating the positions of the instrument to be navigated into those of the coordinate system of the imaging information on the living being or the reconstructed volume of the living being to be employed for the navigation. The markings will usually have to be individually accessed by the instrument if the coordinate transformation between the pair of coordinate systems is to be determined. The markings are also rigidly attached to the living being's body in cases where high-precision medical procedures are involved. Examples that may be mentioned include attaching a stereotactile framework to a patient's head or attaching markings to patients' bones or spinal column. In some cases, the markings are attached in a separate operation, since they have to be attached prior to the preoperative medical imaging that is frequently employed for navigation purposes.

Attachment and registration of the markings is thus a rather unpleasant procedure for patients, and also relatively time-consuming for operators involved in handling preparations for navigation-guided operations.

SUMMARY OF THE INVENTION

The invention thus addresses the problem of creating the prerequisites for a simplified determination of the transformation rule applying to navigation of an instrument, particularly one that employs volumnar data. Other problems that the present invention addresses are those of stating a simplified method for determining the transformation rule without employing markers and of stating a medical system for conducting the method.

The invention solves the first problem by employing an X-ray calibration dummy that has markings that may be acquired by a position-acquisition system as a means of non-marker-based registration when performing navigation-guided operations on an object. Applying such markings to an X-ray calibration dummy creates the prerequisites for determining a transformation relationship between a coordinate system assigned to the X-ray calibration dummy and a coordinate system assigned to an X-ray system for generating the imaging to be employed for navigation purposes with the aid of a position-acquisition system under an offline procedure, for which purpose markings that may be acquired by the position-acquisition system have also been applied to the X-ray system. The X-ray calibration dummy is arranged relative to the X-ray system such that the position and orientation of the coordinate system of the X-ray calibration dummy at least largely coincide with those of the coordinate system of a volume to be reconstructed of a first object employing the X-ray system, or whose position and orientation relative to the coordinate system of the volume to be reconstructed are known. This implies that if the X-ray calibration dummy has been removed and, in general, the positions of the X-ray system and the position-acquisition system relative to one another have been altered in conjunction with the conduct of measurements on an object in comparison to their positions under the offline procedure, the relationship for transforming the coordinate system of the volume to be constructed into a coordinate system of the position-acquisition system may be determined by employing the relationship governing transformation between the coordinate system of the X-ray system and the coordinate system of the volume to be reconstructed and by acquiring the new position of the X-ray system using the position-acquisition system. If the position of a second object to be navigated relative to the first object is then also determined employing the position-acquisition system, then an image of the second object may be inserted into a volume of the first object, which volume has been reconstructed employing measurements on the first object employing the X-ray system, based on the relationship governing the transformations between the coordinate system of the position-acquisition system and the coordinate system of the volume to be reconstructed that has been determined. This implies that the X-ray calibration dummy according to the invention creates the prerequisites for simplifying determination of the rule governing transformation for navigating a second object relative to a first object, while avoiding registration involving markers.

The X-ray calibration dummy of the invention also has additional markings that will appear on X-ray images for determining offline the projection geometries of an X-ray system that may be reproducibly rotated about an axis for the purpose of reconstructing a volumnar record from a series of 2D-projections recorded at various projection angles using the X-ray system. This implies that both the transformation rules needed for navigation and the projection geometries for an X-ray system, i.e., the positions of the X-ray source and the X-ray detector, along with the projection angles and orientations of said X-ray system for every 2D-projection of a series of 2D-projections, knowledge of which is required for reconstructing a volumnar record, may be simultaneously determined under an offline procedure, i.e., prior to conducting any measurements on an object or a patient, with the aid of the X-ray calibration dummy. This in turn implies that, assuming that a suitable X-ray machine is used, for example, an X-ray machine configured in the form of a C-shaped arc, it will create the prerequisites needed for carrying out navigation based on volumnar data generated intraoperatively, without the need for employing any registrations based on markers.

The markings that may be acquired by a position-acquisition system will be arranged within a first zone of the X-ray calibration dummy and the markings that will appear on X-ray images will be arranged within a second zone of the X-ray calibration dummy that differs from the first zone of the X-ray calibration dummy, such that the determination of the transformation rules needed for the navigation will not be adversely affected by the markings that will appear on X-ray images and the determination of the projection geometries will not be adversely affected by the markings that may be acquired by the position-acquisition system.

According to one embodiment of the invention, the X-ray calibration dummy has a cylindrical shape, the first zone being one of the ends of the cylindrically shaped X-ray calibration dummy and the second zone being the lateral surface of same. According to one variant of the invention, the markings that may be acquired by the position-acquisition system are arranged on at last one marker plate attached to the X-ray calibration dummy, which marker plate is usually part of the position-acquisition system.

Another variant of the invention provides for the markings on the X-ray calibration dummy that will appear on X-ray images to be arranged in the form of a helix. Arranging the markings in the form of a helix has proven beneficial in conjunction with determining the projection geometries in the sense that only relatively few overlappings of the markings of the first zone occur on the 2D-projections for determining the projection geometries.

An X-ray calibration dummy that has a helical arrangement of markings that will appear on X-ray images for determining projection geometries is also known from U.S. Pat. No. 5,442,674.

The second problem addressed by the invention is solved by a method of non-marker-based registration for use in navigation-guided operations employing a position-acquisition system, an X-ray machine and an X-ray calibration dummy, the X-ray machine and the X-ray calibration dummy being provided with markings that may be acquired by the position-acquisition system, having the following method steps:

a) orienting the X-ray machine and the X-ray calibration dummy relative to one another such that a coordinate system assigned to the X-ray calibration dummy at least largely coincides with a coordinate system of a volume to be reconstructed of a first object, where the first object is to be X-rayed by the X-ray machine in a subsequent measurement on the first object, or such that the positions of the coordinate systems relative to one another is either known or may be determined in a simple manner, b) determining the position and orientation of the coordinate system of the X-ray calibration dummy or of the volume to be reconstructed and of a coordinate system assigned to the X-ray machine with the position-acquisition system, and c) determining the transformation relationship between the coordinate system of the X-ray machine and the coordinate system of the X-ray calibration dummy or the volume to be reconstructed.

As already mentioned above, if, in conjunction with measurement on an object, the X-ray calibration dummy is removed and the positions of the X-ray machine and the position-acquisition system relative to one another have changed compared to their positions during the offline procedure, the transformation relationship between the coordinate system of the volume to be reconstructed or the coordinate system of the reconstructed volume and a coordinate system of the position-acquisition system may be determined by employing the transformation relationship between the coordinate system of the X-ray system and the coordinate system of the volume reconstructed employing the X-ray machine that has been determined and by acquiring the new position of the X-ray system employing the position-acquisition system.

If finally, according to one variant of the invention, the position of a second object, e.g., an instrument, to be navigated relative to the first object is also acquired employing the position-acquisition system, the transformation relationship between the coordinate system of the position-acquisition system and the coordinate system of the volume to be reconstructed that has been determined following measurement on an object will allow an image of the instrument to be inserted into a volume that has been reconstructed employing the X-ray machine.

One embodiment of the invention provides for the first object to be positioned on a positioning mechanism that is provided with markings that may be acquired by the position-acquisition system, the position of the positioning mechanism being acquired employing the position-acquisition system and a transformation relationship between a coordinate system assigned to the positioning mechanism and the coordinate system of the X-ray calibration dummy or the coordinate system of the volume to be reconstructed is determined. This embodiment of the invention will be beneficial if the X-ray machine is removed from the positioning mechanism during the navigation-guided operation and there is the risk of the position of the position-acquisition system changing relative to the reconstructed volume due to, for example, an unintentional shift. In this case, the positioning mechanism provided with the markings will form a fixed point that may be employed for generating a relation between the coordinate system of the position-acquisition system and the coordinate system of the reconstructed volume.

Another variant of the invention provides for the first object to be provided with markings that may be acquired by the position-acquisition system during the navigation-guided operation. This will be of benefit if there is the risk of the position of the first object on the positioning mechanism changing. There would then no longer be a fixed point that would allow the determination of a transformation relationship between the coordinate system of the position-acquisition system and the coordinate system of the volume to be reconstructed or that has already been reconstructed following removal of the X-ray machine from the positioning mechanism and a shift in the position of the position-acquisition system. If, however, markings that may be acquired by the position-acquisition system are arranged on the first object itself, then a transformation relationship between a coordinate system assigned to the first object and the coordinate system of the volume to be reconstructed of the first object may be determined. This implies that, by determining the position of the first object, a transformation relationship between the position-acquisition system and the coordinate system of the volume to be reconstructed or that has already been reconstructed may be determined based on the transformation relationship between the coordinate system of the first object and the coordinate system of the volume to be reconstructed or that has already been reconstructed of the first object that has been determined, even following a change in the position of the first object.

One variant of the invention provides that, in addition to the markings that may be acquired by the position-acquisition system, the X-ray calibration dummy also has markings that will appear on X-ray images, in order that the projection geometries of the X-ray machine to be employed for reconstructing a volumnar record of the first object from recorded 2D-projections of the first object may be determined simultaneously with the determination of the transformation relationships under the offline procedure. This creates the prerequisites for carrying out navigation without registration involving markers, based on intra-operatively generated volumnar data.

The third problem addressed by the invention is solved by way of a medical system having a position-acquisition system, an X-ray machine and an X-ray calibration dummy, the X-ray machine and the X-ray calibration dummy being provided with markings that may be acquired by the position-acquisition system, it being possible for the X-ray machine and the X-ray calibration dummy also to be oriented relative to one another in a calibration procedure such that a transformation relationship between a coordinate system inscribed on the X-ray calibration dummy or a coordinate system of a volume to be reconstructed of an object to be subsequently X-rayed in conjunction with measurements on the object employing the X-ray machine and a coordinate system assigned to the X-ray machine may be determined with the aid of the position-acquisition system. Said medical system allows both determining of transformation relationships as described above and navigating of an object relative to a volume to be reconstructed.

One variant of the invention provides for the medical system to also have a positioning mechanism that has markings that may be acquired by the position-acquisition system for positioning an object to be examined. As has also been mentioned above, this approach makes it possible to determine a transformation relationship between the coordinate system of the reconstructed volume and the coordinate system of the position-acquisition system in the event that the X-ray machine is removed from the positioning mechanism and the position-acquisition system is unintentionally shifted, for example, during an operation on a patient, if the transformation relationship between the coordinate system of the positioning mechanism and the coordinate system of the volume to be reconstructed has been previously determined.

BRIEF DESCRIPTION OF THE DRAWINGS

An exemplary embodiment of the invention is illustrated in the accompanying schematic drawings, in which.

DESCRIPTION OF THE PREFERRED EMBODIMENTS

Figure 1:
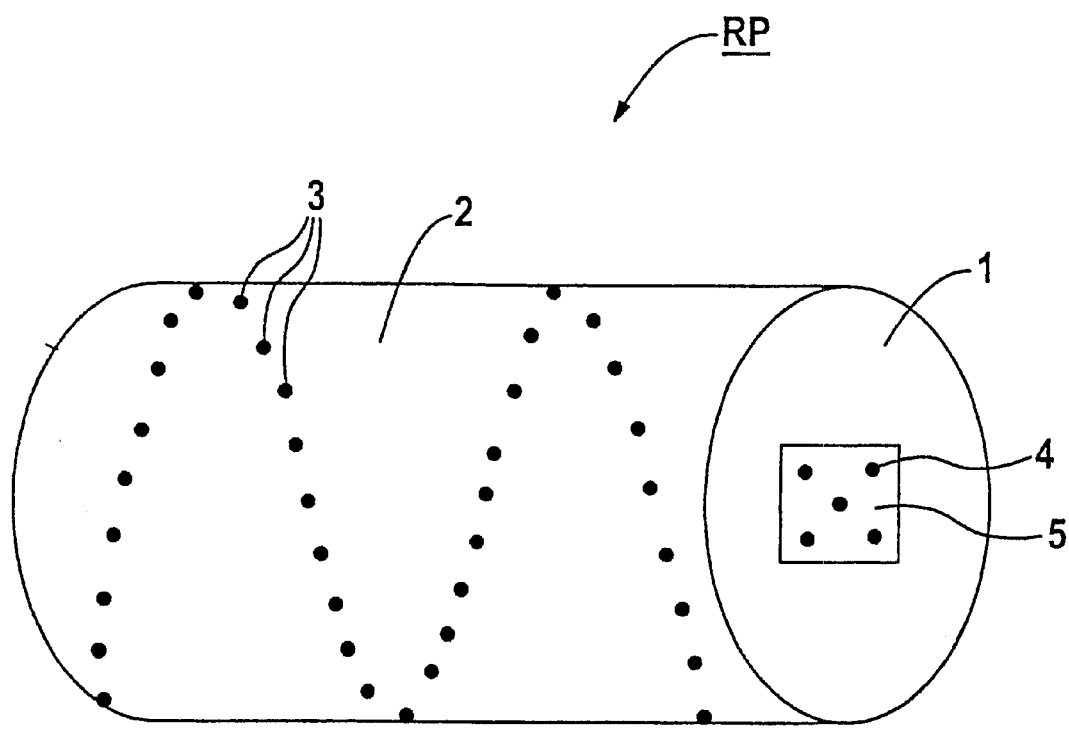
FIG. 1 shows an X-ray calibration dummy conforming to the invention.

FIG. 1 depicts an X-ray calibration dummy, RP, conforming to the invention that has a first zone 1 provided with markings, 4, that may be acquired by a position-acquisition system and a second zone 2 provided with markings, 3, that will appear on X-ray images.

In the case of the present exemplary embodiment, the X-ray calibration dummy RP is configured in the form of a cylinder, one of the ends of the cylinder forming the first zone 1, provided with the markings 4 that may be acquired by a position-acquisition system, and the lateral surface of the cylinder forming the second region 2, provided with the markings 3 that will appear on X-ray images.

Although the markings, 3, that will appear on X-ray images that appear in the second zone, 2, are arranged in the form of a helix, in the case of this exemplary embodiment, the markings, 4, that may be acquired by a position-acquisition system are arranged on a marker plate, 5, attached to the end, 2. In the case of this exemplary embodiment, the markings, 4, are optically detectable markings, 4, preferably optically active elements, such as light sources, which might also be infrared light sources, where the marker plate, 5, is part of an optical position-acquisition system.

Figure 3:
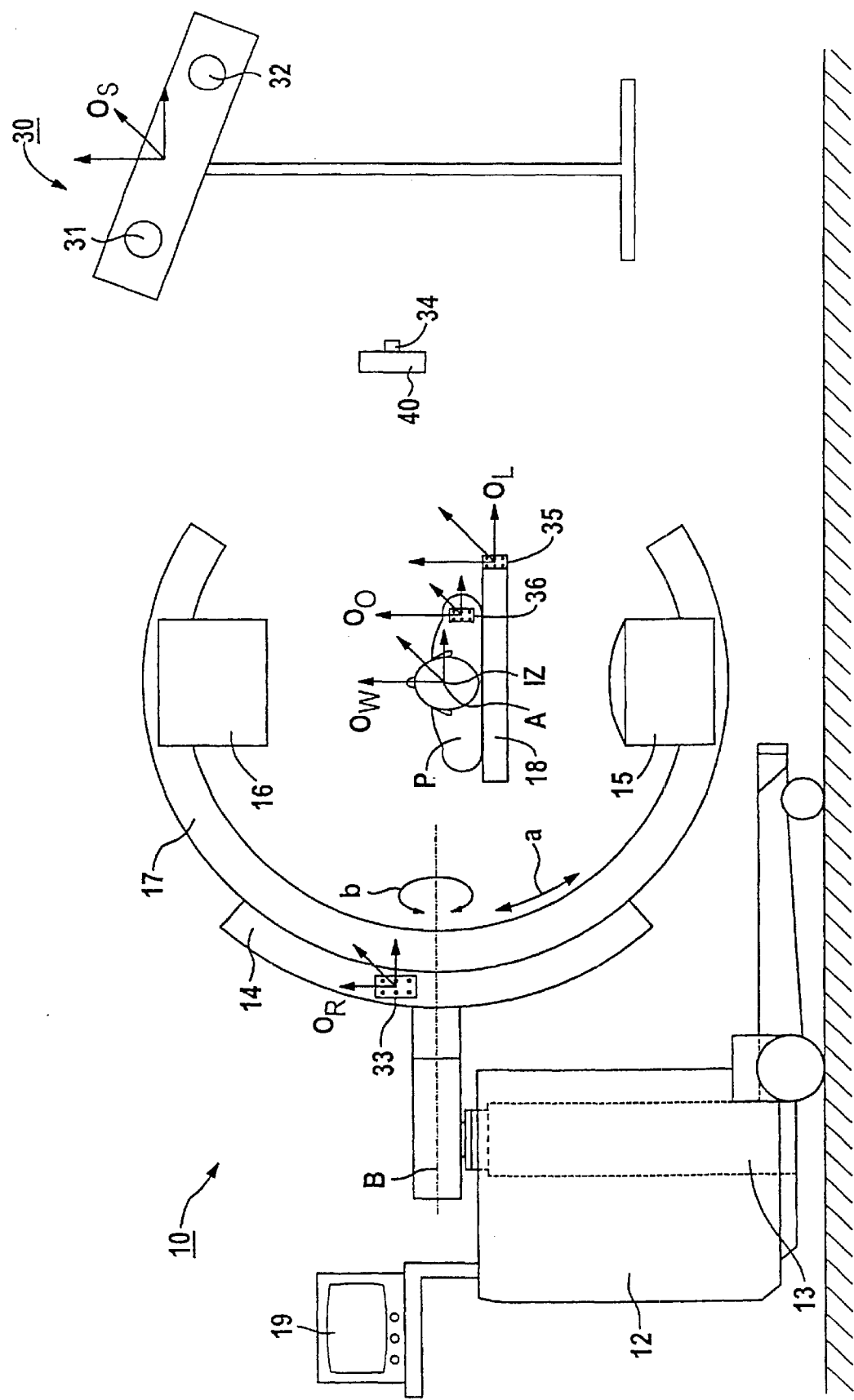
FIG. 3 shows the navigation of an instrument relative to a patient P.

The X-ray calibration dummy, RP, depicted in FIG. 1 is intended for non-marker-based registration under an offline procedure for use in navigation-guided operations on an object, in the case of this exemplary embodiment, on a patient, P, shown in FIG. 3. Said navigation is to take place using X-ray images supplied by an X-ray machine, preferably using a volumnar record supplied by an X-ray machine configured in the form of a C-shaped arc. Another use of the X-ray calibration dummy, RP, is offline determination of the projection geometries of a reproducibly rotatable, motor-driven X-ray system, for example, the X-ray system of the X-ray system configured in the form of a C-shaped arc, for the purpose of reconstructing a volumnar record of a portion of the tissues of the patient, P, from 2D-projections of the portion of the tissues recorded by the X-ray system that have been obtained by rotating the C-shaped arc about its axis and relative to the portion of the tissues.

In order that the offline determination of the projection geometries, for which the markings, 3, that will appear on X-ray images have been employed, will not be adversely affected by the markings that may be acquired by a position-acquisition system employed for the non-marker-based registration, and vice versa, the markings, 3, that will appear on X-ray images and the markings, 4, that may be acquired by the position-acquisition system are arranged over two spatially separated zones, 1 and 2, of the X-ray calibration dummy, RP.

Figure 2:
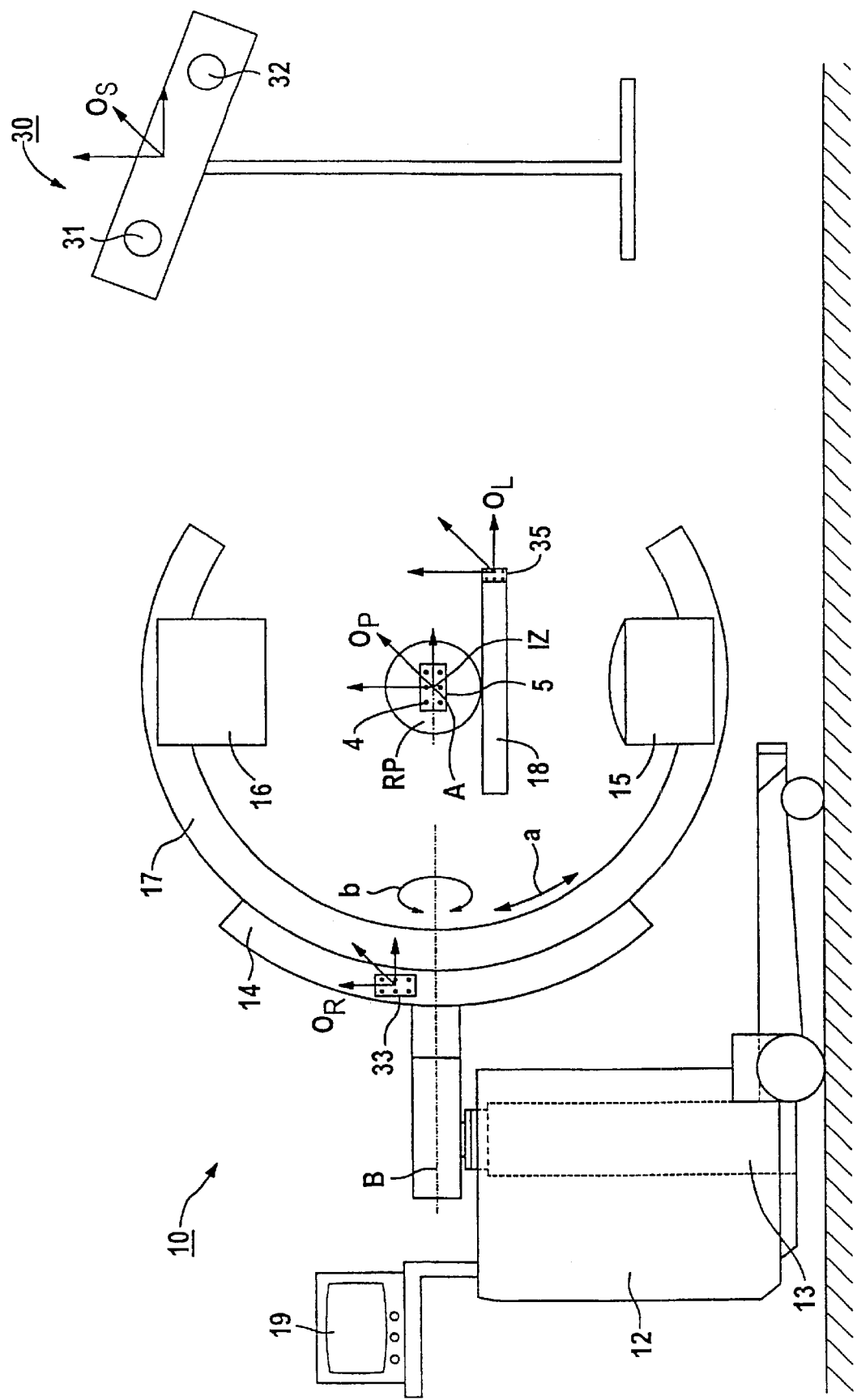
FIG. 2 shows the use of the X-ray calibration dummy from FIG. 1 for non-marker-based registration for use in navigation-guided operations.

FIG. 2 depicts the use of the X-ray calibration dummy, RP, for non-marker-based registration for use in navigation-guided operations employing, in the case of this exemplary embodiment, a translatable X-ray machine, 10, configured in the form of a C-shaped arc, and for determining the projection geometries of the translatable X-ray machine, 10, configured in the form of a C-shaped arc under an offline procedure.

Said X-ray machine, 10, which is known per se and configured in the form of a C-shaped arc is having an equipment cart, 12, having a lifting mechanism, 13, to which a bearing part, 14, is attached. Mounted on the bearing part, 14, is a C-shaped arc, 17, equipped with an X-ray source, 15, and an X-ray detector, 16, which, in the case of the exemplary embodiment shown here, can be adjusted isocentrically over its circumference by pivoting it about its orbital axis, A, as indicated by the double-ended arrow, a. Said C-shaped arc, 17, along with the bearing part 14, may also be isocentrically pivoted about its radial axis, B, in the directions indicated by the double-ended arrow, b. All of the motions of the X-ray system comprising the C-shaped arc, 17, the X-ray source, 15, and the X-ray detector, 16, are reproducible.

FIG. 2 also depicts the optical position-acquisition system, 30, mentioned above, which has a camera system consisting of a pair of cameras, 31 and 32, that are also capable of recording infrared signals, the marker plate, 5, arranged on the X-ray calibration dummy, RP, in the case of this exemplary embodiment, a marker plate, 33, arranged on the bearing part, 14, of the C-shaped X-ray machine, 10, a marker plate, 35, arranged on a patient-positioning mechanism, 18, a marker plate, 36, shown in FIG. 3, arranged on a patient, P, and a position sensor, 34, shown in FIG. 3, attached to a medical instrument, 40. The positions and orientations of the marker plate, 5, and thus those of the X-ray calibration dummy, RP, those of the marker plate, 35, and thus those of the patient-positioning system, 18, those of the marker plate, 36, and thus of the patient, P, those of the position sensor, 34, and thus those of the instrument, 40, and those of the marker plate, 33, and thus those of the bearing part, 14, of the C-shaped X-ray machine, 10, may be determined with the aid of the position-acquisition system, 30. In the case of this exemplary embodiment, each of the respective marker plates involved and the position sensor all bear the same optically detectable markings.

The computing equipment of the position-acquisition system, 30, e.g., a commercially available computer, needed for determining positions is constructed in a manner known per se, and is thus in FIGS. 2 and 3 neither illustrated nor explicitly described.

A navigation-guided operation on the patient, P, shown in FIG. 3, in which an operator, not shown in FIG. 3, guides the medical instrument, 40, equipped with the position sensor, 34, of the position-acquisition system, 30, relative to the patient, P, based on, for example, a reconstructed volume of a portion of the tissues of the patient, P, displayed on a display device, 19, into which an image of the instrument, 40, has been inserted may be performed with the aid of the position-acquisition system, 30. The reconstructed volume of the patient, P, for use in the navigation-guided operation is preferably obtained intraoperatively, that is, during conduct of the medical operation on the patient, P, using the C-shaped X-ray machine, 10.

However, knowledge of the coordinate transformation between the coordinate system, $O_W$, inscribed on the volume of the patient, P, to be reconstructed or that has already been reconstructed and the coordinate system employed for stating the coordinates of the instrument, 40, whose determination under an offline procedure is described below with reference to FIG. 2, is required in order to be able to perform a navigation-guided operation.

The coordinate system, $O_R$, is inscribed on the marker plate, 33, mounted on the bearing part, 14, the coordinate system, $O_L$, is inscribed on the marker plate, 35, arranged on the patient-positioning mechanism, 18, the coordinate system, $O_S$, is inscribed on the camera system of the position-acquisition system, 30, and the coordinate system, $O_P$, is inscribed on the X-ray calibration dummy, RP. Said C-shaped X-ray machine, 10, and, in the case of this exemplary embodiment, the X-ray calibration dummy, RP, positioned on the patient-positioning mechanism, 18, are oriented relative to one another such that the position and orientation of the coordinate system, $O_P$, inscribed on the X-ray calibration dummy, RP, at least largely coincide with those of the coordinate system, $O_W$, of the volume to be subsequently reconstructed in a patient measurement using the C-shaped X-ray machine, 10, which, in the case of this exemplary embodiment, will be a portion of the tissues of the patient, P. Alternatively, the X-ray calibration dummy, RP, may also only be oriented relative to the C-shaped X-ray machine, 10, such that the positions of the pair of coordinate systems relative to one another, that is, the position of the coordinate system, $O_P$, of the X-ray calibration dummy, RP, relative to that of the coordinate system, $O_W$, of the volume to be reconstructed, are known. Since, in the case of this exemplary embodiment, the C-shaped arc, 17, is isocentrically and reproducibly adjustable, the X-ray calibration dummy, RP, as well as the patient, P, during subsequent measurements to be performed on the latter, are preferably oriented such that the origin of the coordinate system, $O_P$, of the X-ray calibration dummy, RP, lies at the isocenter, IZ, of the C-shaped arc, 17, or such that, in the case of measurements on patients, the origin of the coordinate system, $O_W$, lies at the isocenter, IZ, of the C-shaped arc, 17, where the isocenter, IZ, may be marked for identification using, for example, laser beams, during the offline procedure.

Once the C-shaped X-ray machine, 10, and the X-ray calibration dummy, RP, have been oriented relative to one another, the position and orientation of the X-ray calibration dummy, RP, equipped with the marker plate, 5, and the position and orientation of the bearing part, 14, equipped with the marker plate, 33, are determined with the aid of the position-acquisition system, 30, from which a transformation relationship between the coordinate system, $O_P$, of the X-ray calibration dummy, RP, and thus the coordinate system, $O_W$, of the volume to be subsequently reconstructed, and the coordinate system, $O_R$, of the C-shaped X-ray machine, 10, is determined. In the case of measurements on a patient, that is, subsequent to the offline procedure, i.e., following removal of the X-ray calibration dummy, RP, and readjustment of the camera system of the position-acquisition system, 30, and the C-shaped X-ray machine, 10, relative to one another, and following orientation of the coordinate system, $O_W$, inscribed on the volume to be reconstructed of the patient, P, relative to the C-shaped X-ray machine, 10, which corresponds to the orientation of the coordinate system, $O_P$, under the offline procedure, said determination will also make it possible to determine a transformation relationship between the coordinate system, $O_W$, of the volume to be reconstructed of the patient, P, and the coordinate system, $O_S$, of the position-acquisition system, 30, by acquiring the new position of the C-shaped X-ray machine, 10, using the position-acquisition system, 30, and employing the previously determined transformation relationship between the coordinate system, $O_R$, of the C-shaped X-ray machine, 10, and the coordinate system, $O_P$, of the X-ray calibration dummy, RP, or the coordinate system, $O_W$, of the volume to be reconstructed. Finally, if the position of the instrument, 40, within the coordinate system, $O_S$, is determined with the aid of the position-acquisition system, 30, then an image of the instrument, 40, may be inserted into the volume to be reconstructed or that has already been reconstructed, based on the known transformation relationship between the coordinate system, $O_S$, of the position-acquisition system and the coordinate system, $O_W$, of the volume to be reconstructed.

The above makes it clear that the X-ray calibration dummy, RP, according to the invention creates the prerequisites for non-marker-based registration for use in navigation-guided operations on an object.

The transformation relationship between the coordinate system, $O_P$, of the X-ray calibration dummy, RP, or the coordinate system, $O_W$, of the volume to be reconstructed and the coordinate system, $O_L$, of the patient-positioning mechanism, 18, may be determined using the position-acquisition mechanism, 30, in a further process step conducted under the offline procedure. Said transformation relationship will then preferentially be employed only for navigation purposes in cases where the C-shaped X-ray machine, 10, has been removed from the patient-positioning mechanism, 18, and thus from the patient, P, and the position-acquisition system, 30, has been simultaneously shifted relative to the patient, P. In order again to be able to generate a transformation relationship between the volume to be reconstructed or that has already been reconstructed and the position-acquisition system, 30, in this case, the position of the patient-positioning mechanism, 18, is determined using the position-acquisition system, 30, in order that the transformation relationship between the coordinate system, $O_S$, of the position-acquisition system, 30, and the coordinate system, $O_W$, of the reconstructed volume may be determined in a simple manner during an operation, based on the transformation relationship between the coordinate system, $O_P$, of the X-ray calibration dummy, RP, or the coordinate system, $O_W$, of the volume to be reconstructed and the coordinate system, $O_L$, of the patient-positioning mechanism, 18, determined under the offline procedure.

Generating a transformation relationship of this type will also be possible if a marker plate, 36, bearing markings that may be acquired by the position-acquisition system, 30, is attached to an uncritical location on the body of the patient, P, that may be arranged outside that portion of tissue to be treated. This will be beneficial if there is the risk that the patient, P, may alter his/her position on the patient-positioning mechanism, 18, in which case, no fixed point that would allow determining a transformation relationship between the coordinate system, $O_S$, of the position-acquisition system, 30, and the coordinate system, $O_W$, of the volume to be reconstructed or removal that has already been reconstructed would exist any longer following removal of the C-shaped X-ray machine, 10, from the patient-positioning mechanism, 18, and shifting the position of the camera system of the position-acquisition system, 30. However, arranging the marker plate, 36, on the patient, P, also makes this possible under these circumstances, since a transformation relationship between a coordinate system, $O_O$, assigned to the marker plate, 36, and thus assigned to the patient, P, and the coordinate system, $O_W$, of the volume to be reconstructed of the patient, P, may be determined. It follows from this that a transformation relationship between the coordinate system, $O_S$, of the position-acquisition system, 30, and the coordinate system, $O_W$, of the volume to be reconstructed or that has already been reconstructed of the patient P based on the transformation relationship that has been determined between the coordinate system, $O_O$, of the patient, P, and the coordinate system, $O_W$, of the volume to be reconstructed or that has already been reconstructed of the patient P may be determined by acquiring the position of the patient, P, even following a change in the position of the patient, P.

Determination of the projection geometries, knowledge of these being a prerequisite for reconstruction a volume of the patient, P, from a series of 2D-projections obtained using the C-shaped X-ray machine, 10, also takes place in the offline procedure, and more particularly based on the markings, 3, of the X-ray calibration dummy, RP, that will appear on X-ray images. The determination is conducted in a manner known per se.

Non-marker-based registration and determination of the projection geometries also take place under an offline procedure, where the position of the X-ray calibration dummy is not altered during the offline procedure.

Finally, the transformation rules determined under the offline procedure and the projection geometries are stored in a data-storage facility (not shown) for later use in, for example, medical applications like that depicted in FIG. 3.

It follows from the above that a volumnar record of a portion of tissue of the patient, P, who is schematically depicted in FIG. 3 and positioned on the patient-positioning mechanism, 18, may be obtained intraoperatively and displayed in the desired form on a display device, 19, using the C-shaped X-ray machine, 10. The volumnar record is determined intraoperatively from a series of 2D-projections that have been obtained, for example, by rotating the C-shaped arc, 17, about its orbital axis, A, making use of the projection geometries determined under the offline procedure. The items of equipment needed for this purpose, in particular an image-processing computer, are constructed in a manner known per se and are thus not shown in FIGS. 2 and 3 and are not explicitly described.

With the aid of the transformation rules that have been determined and the volumnar record that has been determined intraoperatively, intraoperative navigation of the instrument, 40, relative to that portion of tissue of the patient, P, depicted in the volumnar record is thus possible.

The configuration of the X-ray calibration dummy, RP, described above should moreover only be taken as an example. Said X-ray calibration dummy thus need not have a cylindrical shape. On the contrary, the X-ray calibration dummy may also have any other suitable shape.

Said position-acquisition system need not be an optical position-acquisition system that operates with optical waves. On the contrary, position-acquisition systems that operate with electromagnetic waves or acoustic waves are also suitable. Electromagnetic position-acquisition systems are equipped with devices for transmitting and for receiving electromagnetic waves. Similarly, acoustic position-acquisition systems are equipped with acoustic wave transmitters and acoustic wave receivers. Said transmitters of the position-acquisition systems are preferably attachable to those moving objects whose positions are to be determined, while the receivers are permanently mounted in relation to the transmitters. However, it is also possible to fixedly arrange the receivers on the moving objects and to fixedly arrange the transmitters in relation to the receivers.

What is claimed is:

1. An X-ray calibration dummy comprising:
   first markings (3) that will appear on X-ray images for use in determining projection geometries of an X-ray system that may be rotated about an axis (A) used for reconstructing a volumnar record; and
   second markings (4) differing from the first markings (3) and that may be acquired by a position-acquisition system (30) for non-marker-based registration for use in navigation guided operations on an object (P),
   the second markings (4) being arranged within a first zone (1) of the X-ray calibration dummy (RP) and the first markings (3) being arranged within a second zone (2) of said X-ray calibration dummy that differs from the first zone (1), wherein said X-ray calibration dummy (RP) has a cylindrical shape, the first zone (1) being one of the ends of the cylindrically shaped X-ray calibration dummy (RP) and the second zone (2) being a lateral surface of the cylindrically shaped X-ray calibration dummy.

2. The X-ray calibration dummy as claimed in claim 1, in which the first markings (3) are arranged in the form of a helix.

3. The X-ray calibration dummy as claimed in claim 1, in which the second markings (4) are arranged on at least one marker plate (5) attached to said one of the ends of the cylindrically shaped X-ray calibration dummy (RP).

4. A method for non-marker-based registration for use in navigation-guided operations employing a position-acquisition system (30), an X-ray machine (10) and an X-ray calibration dummy (RP), the X-ray machine (10) and the X-ray calibration dummy (RP) being provided with markings (4, 33) that may be acquired by the position-acquisition system (30), having the following method steps:

a) orienting the X-ray machine (10) and the X-ray calibration dummy (RP) relative to one another such that a coordinate system ($O_P$) assigned to the X-ray calibration dummy (RP) at least largely coincides with coordinate system ($O_W$) of a volume to be reconstructed of a first object (P) to be X-rayed by the X-ray machine (10) in a subsequent measurement on the object (P) or such that the positions of both of the coordinate systems, ($O_P$ and $O_W$) relative to one another are either known or may be determined in a simple manner, b) determining the position and orientation of the coordinate system ($O_P$) of the X-ray calibration dummy (RP) or the coordinate system $O_W$ of the volume to be reconstructed and of a coordinate system ($O_R$) assigned to the X-ray machine (10) and c) determining the transformation relationship between the coordinate system ($O_R$) of the X-ray machine (10) and the coordinate system ($O_P$) of the X-ray calibration dummy (RP) or the coordinate system ($O_W$) of the volume to be reconstructed.

5. The method as claimed in claim 4, in which the markings, 4, that may be acquired by the position-acquisition system (30) are arranged on a marker plate (5, 33, 35) attached to the X-ray calibration dummy (RP), to the X-ray machine (10) and/or to the positioning mechanism (18) respectively.

6. The method as claimed in claim 4, in which the position of a second object (40) to be navigated relative to the first object (P) is acquired by the position-acquisition system (30).

7. The method as claimed in claim 5, in which a positioning mechanism (18) for positioning the first object (P) that has markings (35) that may be acquired by the position-acquisition system (30), the position of the positioning mechanism (18) being acquired by the position-acquisition system, 30, and a transformation relationship between a coordinate system ($O_L$) assigned to the positioning mechanism (18) and the coordinate system ($O_P$) of the X-ray calibration dummy (RP) or the coordinate system ($O_W$) of the volume to be reconstructed is determined.

8. The method as claimed in claim 5, in which the first object (P) is provided with markings (36) that may be acquired by the position-acquisition system (30) the position of the first object (P) being acquired by the position-acquisition system (30) and a transformation relationship between a coordinate system ($O_O$) assigned to the first object (P) and the coordinate system ($O_W$) of the volume to be reconstructed is determined.

9. The method as claimed in claim 5, in which, in addition to the markings (4) that may be acquired by the position-acquisition system (30) the X-ray calibration dummy (RP) also has markings (3) that will appear on X-ray images, an offline determination of the projection geometries of the X-ray machine (10) employed for reconstructing a volumnar record of the first object (P) from recorded 2D-projections of the first object (P) also taking place.

10. The method as claimed in claim 9, in which the X-ray calibration dummy (RP) has a cylindrical shape, the markings (3) that will appear on X-ray images being arranged in the form of a helix extending around the lateral surface (2) and at least one of the ends (1) being provided with markings (4) that may be acquired by the position-acquisition system (30).

11. The method as claimed in claim 4, in which the X-ray machine is an adjustable C-shaped X-ray machine (10).

12. The method as claimed in claim 11, in which the C-shaped arc (17) of the C-shaped X-ray machine (10) is isocentrically adjustable.

13. A medical system comprising:

a position-acquisition system (30), an adjustable C-shaped X-ray machine (10), and an X-ray calibration dummy (RP), the X-ray calibration dummy (RP) having first markings (3) that will appear on X-ray images, the X-ray machine (10) and the X-ray calibration dummy (RP) being provided with second markings (4) that may be acquired by the position-acquisition system (30), the X-ray machine (10) and the X-ray calibration dummy (RP) being orientable relative to one another in a calibration operation such that a transformation relationship between a coordinate system ($O_p$) inscribed on the X-ray calibration dummy (RP) or a coordinate system ($O_w$) of a volume to be reconstructed of an object (P) to be X-rayed by the X-ray machine (10) in a subsequent measurement on the object (P) and a coordinate system ($O_R$) assigned to the X-ray machine (10) may be determined with the aid of the position-acquisition system (30), wherein the X-ray calibration dummy (RP) has a cylindrical shape, the first markings (3) being arranged in the form of a helix extending around a lateral surface (2) of the cylindrical shape and at least one of end (1) of the cylindrical shape having the second markings (4).

14. The medical system as claimed in claim 13, in which the C-shaped arc (17) of the X-ray machine (10) is isocentrically adjustable.

15. The medical system as claimed in claim 13 having a positioning mechanism (18) for positioning the object (P) which positioning mechanism is provided with third markings (35) that may be acquired by the position-acquisition system (30) such that the position of the positioning mechanism (18) may be acquired by the position-acquisition system (30).

16. The medical system as claimed in claim 13, in which the second markings are arranged on a marker plate (5, 33, 35) attached to the at least one end of the X-ray calibration dummy (RP).

* * * * *